US 8,825,136 B2

(12) United States Patent
Giller et al.

(10) Patent No.: US 8,825,136 B2
(45) Date of Patent: Sep. 2, 2014

(54) SYSTEM AND METHOD FOR PRE-PLANNING A RADIATION TREATMENT

(75) Inventors: Cole A. Giller, Dallas, TX (US); Jeffrey A. Fiedler, Dallas, TX (US)

(73) Assignee: Baylor Research Institute, Dallas, TX (US)

(*) Notice: Subject to any disclaimer, the term of this patent is extended or adjusted under 35 U.S.C. 154(b) by 769 days.

(21) Appl. No.: 12/397,881

(22) Filed: Mar. 4, 2009
(Under 37 CFR 1.47)

(65) Prior Publication Data
US 2010/0056908 A1 Mar. 4, 2010

Related U.S. Application Data (60) Provisional application No. 61/036,821, filed on Mar. 14, 2008.

(51) Int. Cl.
*A61B 5/05* (2006.01)
(52) U.S. Cl.
USPC ........... 600/425; 600/407; 600/426; 600/427; 600/429
(58) Field of Classification Search
USPC .................... 600/407, 425, 426, 427, 429
See application file for complete search history.

(56) References Cited

U.S. PATENT DOCUMENTS

| 4,827,491 A * | 5/1989 | Barish ........................... 378/65 |
| 5,027,818 A * | 7/1991 | Bova et al. ..................... 600/427 |
| 5,205,289 A * | 4/1993 | Hardy et al. .................. 600/429 |
| 5,373,844 A * | 12/1994 | Smith et al. ................... 600/427 |
| 5,458,125 A * | 10/1995 | Schweikard .................. 600/407 |
| 5,784,431 A * | 7/1998 | Kalend et al. .................. 378/65 |
| 6,504,899 B2 | 1/2003 | Pugachev et al. |
| 7,046,762 B2 | 5/2006 | Lee |
| 7,171,257 B2 | 1/2007 | Thomson |
| 7,194,295 B2 | 3/2007 | Vilsmeier |
| 7,260,426 B2 | 8/2007 | Schweikard et al. |
| 7,266,176 B2 | 9/2007 | Allison et al. |
| 7,298,819 B2 | 11/2007 | Dooley et al. |
| 7,302,033 B2 | 11/2007 | Carrano et al. |
| 7,438,685 B2 * | 10/2008 | Burdette et al. .............. 600/439 |
| 7,551,717 B2 * | 6/2009 | Tome et al. ..................... 378/65 |
| 7,831,017 B2 * | 11/2010 | Myles ............................. 378/65 |

(Continued)

OTHER PUBLICATIONS

A survey of medical image registration by J. B. Antoine Maintz, Image Sciences Institute, Utrecht University Hospital, Utrecht, The Netherlands pub. Medical Image Analysis (1998) vol. 2, No. 1, pp. 1-36.*

(Continued)

*Primary Examiner* — Long V. Le
*Assistant Examiner* — Michael Kellogg
(74) *Attorney, Agent, or Firm* — Fulbright & Jaworski LLP (57) ABSTRACT

The present invention includes a method of pre-planning a spherical fixed point stereotactic radiosurgery by obtaining an image from a patient having a target, the image comprising coordinates of the actual patient target in 3 dimensions on a first day; planning an optimal stereotactic radiosurgery using the patient's actual target using actual coordinates in 3 dimensions prior to the day of surgery by creating virtual radiosurgical coordinates and plans to maximize target exposure and minimize the patient's waiting time in radiosurgery, thereby allowing evaluation of several plans to maximize plan conformality and safety; and treating the patient based on the virtual stereotactic radiosurgery plans on a second day.

12 Claims, 12 Drawing Sheets

(56) References Cited

U.S. PATENT DOCUMENTS

| | | | |
|---|---|---|---|
| 2004/0002641 A1 | 1/2004 | Sjogren et al. | |
| 2004/0242991 A1 | 12/2004 | Frohlich et al. | |
| 2005/0049478 A1 | 3/2005 | Kuduvalli et al. | |
| 2005/0080332 A1 | 4/2005 | Shiu et al. | |
| 2006/0291621 A1* | 12/2006 | Yan et al. | 378/65 |
| 2009/0147916 A1* | 6/2009 | Fallone et al. | 378/65 |

OTHER PUBLICATIONS

Stereotactic radiosurgery by Lars Leksell, From the department of neurosurgery, Karolinska Sjukhuset, Stockholm, Sweden pub. Journal od Neurology, Neurosurgery, and Psychiatry 1983; issue 46: p. 797-803.*

Advances and Technical Standards in Neurosurgery vol. 17 Springer-Verlag Wien New York 1990 pp. 77-116.*

Christodouleas, J.P., et al., "Virtual Frame-Guided Gamma Knife Radiosurgery Reduces Multiple Frame Placements and Trunnion Mode Treatments," I.J. Radiation Oncology, Biology, Physics (2007), 69:S648-649 (Abstract).

Ford, E.C., et al., "A Virtual Frame System for Stereotactic Radiosurgery Planning," I.J. Radiation Oncology, Biology, Physics (2007), 69:S660 (Abstract).

Schwartz, M.L., "Frameless stereotaxy for pre-treatment planning and post-treatment evaluation of radiosurgery," Can J Neurol Sci (1994), 21:319-324.

Serra, L., et al., "The Brain Bench: virtual tools for stereotactic frame neurosurgery," Medical Image Analysis (1996), 1:317-329.

* cited by examiner

| Pre-Planning Image Calculated Skull Radii: | | | | | | | | |
|---|---|---|---|---|---|---|---|---|
| TOP: | 75.00 | | | | | | | |
| | 1 | 2 | 3 | 4 | 5 | 6 | 7 | 8 |
| A | 76.8 | | 79.7 | | 76.8 | | 79.7 | |
| B | | 84.7 | | 84.7 | | 84.7 | | 84.7 |
| C | 81.7 | 87.8 | 95.4 | 87.8 | 81.7 | 87.8 | 95.4 | 87.8 |
| D | 81.2 | 86.6 | | 86.6 | 81.2 | 86.6 | 93.2 | 86.6 |

| | Semi x-axis Dimension: 81.75 | | Semi y-axis Dimension: 95.45 | | Semi z-axis Dimension: 75.00 | | | |
|---|---|---|---|---|---|---|---|---|
| α (A) | 87.4 | | 0.0 | | -87.4 | | 0.0 | |
| β (A) | 0.0 | | 87.4 | | 0.0 | | -87.4 | |
| γ (A) | 134.0 | | 134.0 | | 134.0 | | 134.0 | |
| α (B) | | 101.0 | | -101.0 | | -101.0 | | 101.0 |
| β (B) | | 101.0 | | 101.0 | | -101.0 | | -101.0 |
| γ (B) | | 72.0 | | 72.0 | | 72.0 | | 72.0 |
| α (C) | 159.8 | 113.0 | 0.0 | -113.0 | -159.8 | -113.0 | 0.0 | 113.0 |
| β (C) | 0.0 | 113.0 | 159.8 | 113.0 | 0.0 | -113.0 | -159.8 | -113.0 |
| γ (C) | 7.5 | 7.5 | 7.5 | 7.5 | 7.5 | 7.5 | 7.5 | 7.5 |
| α (D) | 153.7 | 108.7 | | -108.7 | -153.7 | -108.7 | 0.0 | 108.7 |
| β (D) | 0.0 | 108.7 | | 108.7 | 0.0 | -108.7 | -153.7 | -108.7 |
| γ (D) | -44.5 | -44.5 | | -44.5 | -44.5 | -44.5 | -44.5 | -44.5 |

SYSTEM AND METHOD FOR PRE-PLANNING A RADIATION TREATMENT

CROSS-REFERENCE TO RELATED APPLICATIONS

This application claims priority to U.S. Provisional Application Ser. No. 61/036,821, filed Mar. 14, 2008, the entire contents of which are incorporated herein by reference.

TECHNICAL FIELD OF THE INVENTION

The present invention relates in general to the field of non-invasive surgical treatments, and more particularly, to a new method for planning radiosurgery.

STATEMENT OF FEDERALLY FUNDED RESEARCH

None.

INCORPORATION-BY-REFERENCE OF MATERIALS FILED ON COMPACT DISC

None.

BACKGROUND OF THE INVENTION

Without limiting the scope of the invention, its background is described in connection with planning for radiosurgery and/or radiation oncology procedures.

One such system is discussed in United States Patent Application No. 20040242991, filed by Frohlich, et al. for a method for determining dosage when planning radiotherapy and/or radiosurgery procedures. Briefly, a method for determining dosage when planning radiotherapy and/or radiosurgery procedures can include imaging an irradiation target area using an imaging method which can differentiate functional and/or biologically active regions of the irradiation target area. The activity values ascertained can be allocated to individual regions of the imaged irradiation target and irradiation doses can be assigned to the regions in accordance with the activity values. Finally, a nominal dosage distribution, which can be ascertained from the irradiation dosages for the regions, can be used as an input value for treatment planning.

Yet another system is taught in United States Patent Application No. 20050049478, filed by Kuduvalli, et al., for an image guided radiosurgery method and apparatus using registration of 2D radiographic images with digitally reconstructed radiographs of 3D scan data. Briefly, an image-guided radiosurgery method and system use 2D/3D image registration to keep the radiosurgical beams properly focused onto a treatment target. Next, a pre-treatment 3D scan of the target is generated at or near treatment planning time and a set of 2D digitally reconstructed radiographs (DRRs) are generated, based on the pre-treatment 3D scan. At least one 2D x-ray image of the target is generated in near real time during treatment and the DRRs are registered with the x-ray images, by computing a set of 3D transformation parameters that represent the change in target position between the 3D scan and the x-ray images. The relative position of the radiosurgical beams and the target is adjusted continuously in near real time in accordance with the 3D transformation parameters. Finally, a hierarchical and iterative 2D/3D registration algorithm is used, in which the transformation parameters that are in-plane with respect to the image plane of the x-ray images are computed separately from the out-of-plane transformation parameters.

SUMMARY OF THE INVENTION

The present invention provides patient and physician several advantages. First, by pre-planning and having the time to design various treatment options, the present inventors have found an increase in the convenience to the patient, including a reduction of waiting time during planning and improved patient care leading to a reduced possibility of needing another treatment. Second, by making possible consideration of various planning strategies that could not otherwise be considered due to the time constraints of radiosurgical procedures, the present invention increases the efficacy of the dosing regime thereby improving patient care. Among the increases in efficacy is a reduced risk of radiotoxicity to adjacent non-target tissues. It has been found that the present invention saves time, allows exploration of planning strategies that would not otherwise be considered, expands the application of the particular radiosurgical software to other radiation therapy machines. Furthermore, the present invention allows the use of optimization algorithms that could not otherwise be used due to the time constraints of Gamma Knife® radiosurgery.

In one embodiment the present invention includes a system and method of pre-planning fixed source stereotactic radiosurgery by obtaining an image from a patient having a target, the image that includes coordinates of the actual patient target in 3 dimensions on a first day; planning an optimal stereotactic radiosurgery using the patient's actual target using actual coordinates in 3 dimensions prior to the day of surgery by creating virtual radiosurgical coordinates and plans to maximize target exposure and minimize the patient's time waiting during radiosurgery planning, thereby allowing evaluation of several plans to maximize plan conformality and safety; and treating the patient based on the information gained during the virtual planning of stereotactic radiosurgery plans on a second day. In one aspect, the method may also include the step of pre-programming one or more surgical plans into the radiosurgical device based on the optimal stereotactic radiosurgery plan prior to stereotactic radiosurgery. In yet another aspect, the image may be either a CT, MRI or PET image. The image may be marked with one or more natural fiducials that include bony or other anatomic landmarks, the surgical target, one or more parts of the frame or one or more pre-positioned markers. The present invention may also include adding a frame in silico.

In another embodiment, the present invention includes a method of pre-planning stereotactic radiosurgery by obtaining one or more images from a patient having a target; adding a stereotactic frame in silico to the one or more images; selecting three or more points from the one or more images centered at the target, therein the three or more points comprise vertices of a right triangle with sides equal to half of the distance between fiducial markers and the center of the stereotactic frame; matching the distances between the fiducial markers and the stereotactic frame; identifying a center slice in the image to define a middle slice of stereotactic space; measuring the length, width and distance to a skull vertex in the image and using parametric formula to calculate the skull radii; and planning an optimal stereotactic radiosurgery treatment using the patient's actual target using actual coordinates in 3 dimensions prior to the day of surgery by creating a set of virtual radiosurgical coordinates and plans, thereby allowing evaluation of several plans to optimize conformality and safety. In one aspect, the method also includes the step of treating the patient based on the optimal stereotactic radiosurgery plan on a second day. In another aspect, the invention includes the step of pre-programming one or more surgical plans into the radiosurgical device based on the optimal stereotactic radiosurgery plan prior to stereotactic radiosurgery. Examples of images for use with the present invention include, but are not limited to, a CT, MRI or PET images or datasets. In another aspect, the image is marked based on one or more natural fiducials including bony or other anatomic landmarks, the surgical target, one or more parts of the frame or one or more pre-positioned markers. In one aspect, the stereotactic radiosurgery is performed using a stereotactic radiation surgical device.

In yet another embodiment, the present invention includes a system and method of pre-planning radiosurgery by obtaining an image from a patient having a surgical target wearing a frame in a linear accelerator stereotactic radiosurgery device, the image comprising coordinates of the actual patient target in 3 dimensions within a virtual frame on a first day; planning an optimal stereotactic radiosurgery using the patient's actual target within the virtual frame using actual coordinates in 3 dimensions prior to the day of surgery by executing virtually several surgical plans using the patient's actual target and virtual frame image, wherein the plan maximizes target exposure and minimizes the patient's waiting time prior to radiosurgery; Pre-programming one or more of the plans into the linear accelerator stereotactic radiosurgery device; and treating the patient on a second day based on the optimal stereotactic radiosurgery plan. In another aspect, the invention also includes the step of pre-programming one or more surgical plans into the radiosurgical device based on the optimal stereotactic radiosurgery plan prior to stereotactic radiosurgery. Examples of images for use with the present invention include, but are not limited to, CT, MRI or PET images or datasets. In another aspect, the image is marked based on one or more natural fiducials that include bony or other anatomic landmarks, the surgical target, one or more parts of the frame or one or more pre-positioned markers. In one aspect, the stereotactic radiosurgery is performed using a stereotactic radiation surgical device.

The present invention also includes the use of in silico framing to establish a stereotactic coordinate system on a tumor being considered for treatment with any linear accelerator system or any fixed source system, then creating and comparing several radiosurgical plans using the virtual coordinates, then translating one of these plans to the other machine for definitive treatment. One advantage of the present invention is an increase in the speed and precision of the sphere packing radiosurgical planning system to derive radiosurgical plans for the other machines that would not otherwise be obvious or available. Another embodiment of the present invention is to establish an in silico frame and coordinates as before, which is then used in conjunction with optimization algorithms to find an optimal radiosurgical plan. These algorithms typically require hours to run and so are not feasible for ordinary fixed source radiosurgeries, which are limited to one day. By allowing plans and runs to occur prior to the day of treatment, virtual framing allows the use of optimization programs that could not otherwise be used due to the extraordinary processing time required by these systems.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention is based on the recognition of the need to pre-plan the series of overlapping targeting events for radiation treatment. It has been found that patient treatment can be improved significantly by having the opportunity to attempt various different treatment modalities in silico prior to providing actual radiation treatments. It has been found that having the opportunity to pre-plan targeting and treatments events, in particular for hard to treat cases such as those targets having highly irregular shapes or close to tissue areas that are highly sensitive to radiation, increases patient outcome and significantly reduces the total time that the patient has to await treatment.

The present invention includes many of the following steps. The skilled artisan will recognize that some of the these steps may be used or eliminated based on actual patient needs, however, the entire set of steps is provided so as to maximize the number of options made available to the treating physicians. First, images of the patient data set are identified. One of the advantages of the present invention is that these can be arbitrary images without need for presence of stereotactic frame. Furthermore, the actual nature of the images is variable, that is, the images can be, for example, cross-sectional tomographic datasets such as Computer Tomography, Magnetic Resonance Imaging, Positron Emission Tomography and Ultrasound. So long as the imaging data shows soft tissues features, it can be used with the present invention. Next, the image of a stereotactic frame is opened in, e.g., Gamma Plan software (the software for the Gamma Knife® system). The skilled artisan will recognize that other software packages are available with the radiation treatment system that they may be using.

Next, three points are chosen on the patient data set so that they are centered at a slice that will correspond to the middle z=100 slice of a Gamma Knife data set, which will preferably be a slice that includes largest right-left and anterior-posterior cranial dimensions and so that they are vertices of a right triangle with sides equal to half of the distance between the outermost fiducials and those at the center of the stereotactic frame. The skilled artisan will recognize that a right triangle is one shape that may be selected, however, so long as the shape and lengths between the points on the shape are known, any length and shape may be used. The image viewer functionality of the software includes tools to measure lengths, which can be used in this step to determine the positions of the points and the distances therebetween. After the three points are chosen on the frame data set, lengths are determined (based on the known geometry of the frame) to match the length to match the three points of the right triangle selected on the patient dataset.

Having obtained, measured and matched the shape and the distances in the software, the two sets of three points (from the image and the fiducials), these points are used to co-register the two data sets using the Gamma Plan software (again, equivalent software packages are available with the other radiation therapy systems). Next, the slice previously chosen in the patient data set is chosen to serve as the middle slice of stereotactic space. A center slice is a convenient, but not a limiting, slice to select to orient and train the software. Using the measuring tools, the length, width and distance to skull vertex is measured on the patient data set. The distances are then entered into a spreadsheet that calculates skull radii using, e.g., the formula described hereinbelow for calculating a skull radii. The skull radii are required for use of the Gamma Plan software and are then entered into the Gamma Plan software and plans developed in the usual fashion.

Now that the images have been co-registered with the fiducials and the three dimensional size for the skull radii have been matched, pre-planning can then take place as usual. While the skull radii is determined based on a formula and not the actual patient radii, it has been found that the calculated radii correlates very well with actual data. Furthermore, if available, actual patient skull radii may be used.

During the preplanning phase, if another enhancement of the radiosurgical device is desired, the radiation shots used to develop the radiation treatment plan may be modified with plug patterns to imitate isocenter plans of other radiation systems. Conversely, modification of the treatment parameters of other radiation systems can be made so that their isocenter plans imitate that of the GAMMA KNIFE®. Furthermore, the skilled artisan will recognize that the present invention is not limited to use with stereotactic radiation treatment systems, methods and equipment, but may also be used with any radiation therapy system or any robotic controlled radiation treatment systems, such as any frameless robotic radiosurgery system, e.g., CYBERKNIFE®. Using the present invention if, e.g., the GAMMA KNIFE® plan is emulated on another device or systems, this may be accomplished by transferring coordinates of each shot to the coordinate space of the device using anatomical landmarks to specify an origin. The plan can then be built from isocentric components of the alternative device.

Other radiosurgical devices that could use the present invention include so-called shaped beam surgery in which a linear accelerator uses a high spatial resolution miniature Multileaf Collimator (mMLC) in conjunction with stereotactic systems and imaging to position and target the tumor or other features in need of surgery during treatment (e.g., vascular malformations). The "beam shaping" capabilities allow the shape of the radiation beam to be optimized for the treatment area.

The in silico frame of the present invention may be used in conjunction with any of the optimization algorithms provided with the various systems and their software packages, or with any ad hoc optimization algorithm, and based on the robust nature of the method and the various uses for the imaging data, the present invention allows for the use of the methodology with various software packages, various machines across platforms.

Calculation of Skull Radii for Virtual Frames.

The skull radii may be calculated as follows. Assuming that the skull is a perfect ellipse centered at the origin, described by:

$$x^2/a^2+y^2/b^2+z^2/c^2=1$$

The hemisphere from which the points of measurement are taken is a sphere of radius 160 mm, also centered at the origin.

Let (x0, y0, z0) be one of these points. Then t(x0, y0, z0) is a line between the origin and this point, where t ranges between 0 and 1. Let te be the value of t at which this line intersects the ellipse. Then:

$$(t_e x_0/a)^2+(t_e y_0/b)^2+(t_e z_0/c)^2=1,$$

i.e., $$t_e=(1/(x_0^2/a^2+y_0^2/b^2+z_0^2/c^2))^{1/2} \quad (1)$$

The skull radius associated with (x0, y0, z0) is therefore:

$$t_e(x_0^2+y_0^2+z_0^2)^{1/2}=160 t_e, \quad (2)$$

because (x0, y0, z0) lies on the above hemisphere.

Skull radii are then calculated from the coordinates of each measurement point on the hemisphere using (1) and (2).

EXAMPLE 1

Sample Treatment Regime

Figure 1:
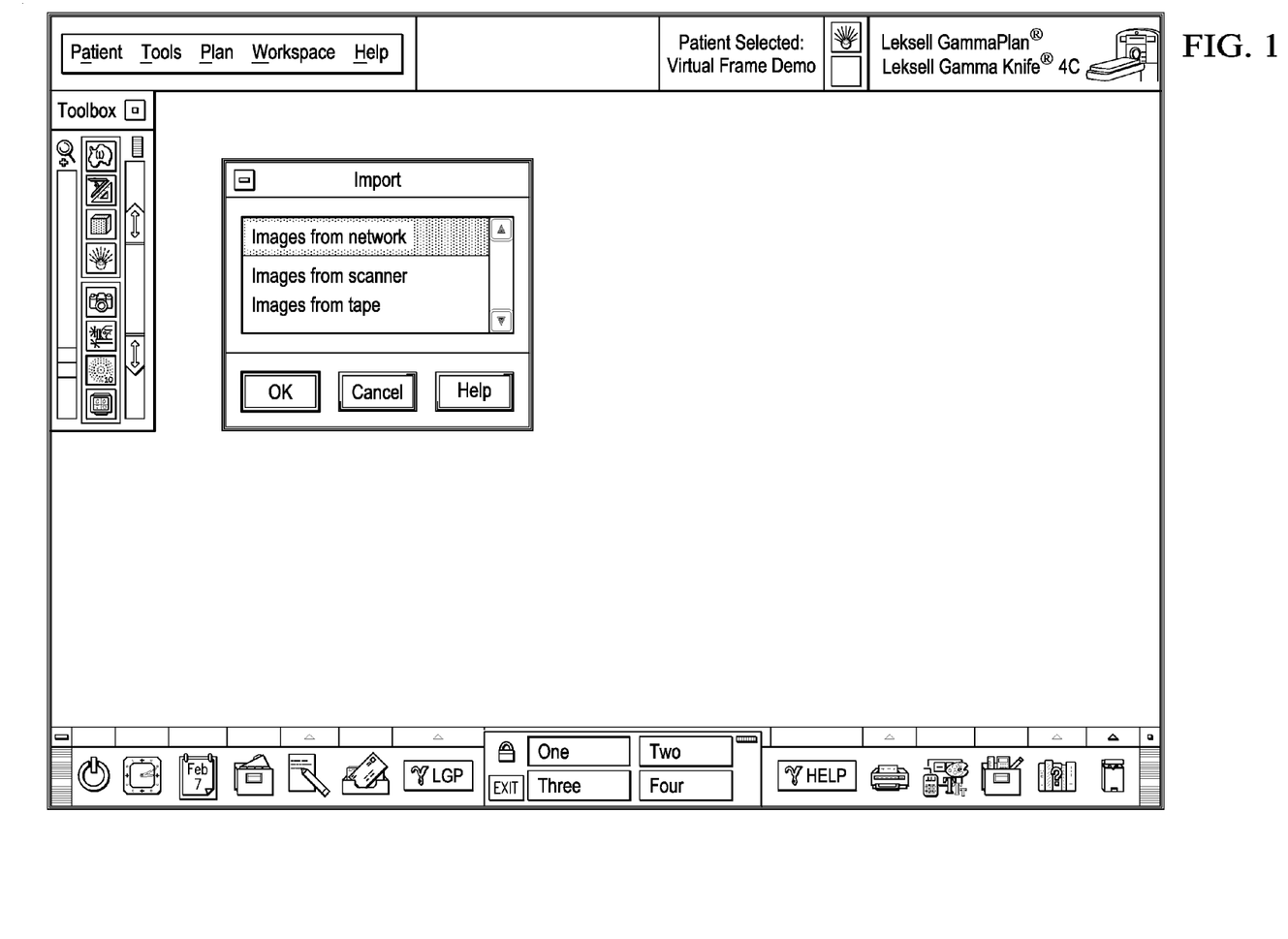
FIG. 1 is a screen shows the Gamma Knife® system menu used to bring the CT of the frame and the patient MRI from the local network.

FIG. 1 is a screen shows the Gamma Knife® menu used to bring the CT of the frame and the patient MRI from the local network. While this example is provided using the Gamma Plan software provided with the system, the skilled artisan will recognize that equivalent functionality is found in the software packages provided with other similar stereotactic radiation treatment equipment. While the screen shots will vary, the manner in which data is loaded, viewed, manipulated and co-registered is substantially the same. In this Figure, the software is ready to load imaging data obtained from the patient.

Figure 2:
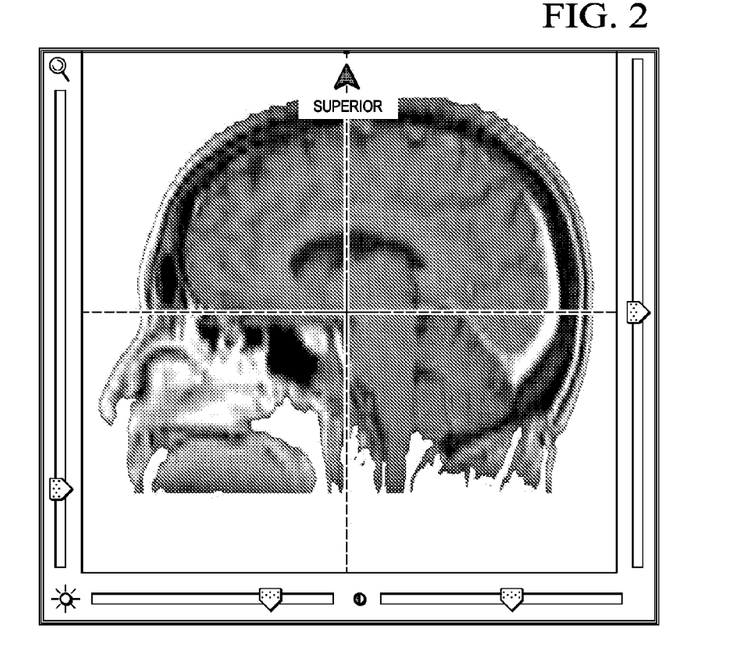
FIG. 2 is a screen shot of a patient MRI that must be oriented correctly using the co-registration software of the Gamma Knife® system. Slices must be contiguous.

FIG. 2 is a screen shot of a frameless patient MRI, which must be oriented correctly using the co-registration software of, in this case, the Gamma Knife®. Generally, the image slices must be contiguous and their amount and thickness known or calculable.

Figure 3:
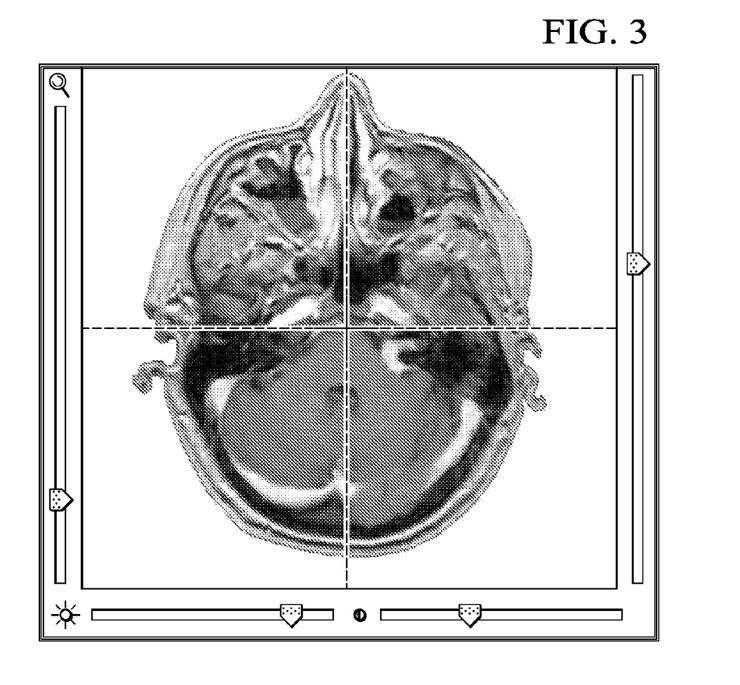
FIG. 3 is a screen shot of MRI data has been successfully imported into the Gamma Knife® system. Note the absence of fiducials.

FIG. 3 is a screen shot of MRI data has been successfully imported into the Gamma Knife system. The skilled artisan will notice the absence of fiducials in the image, as the image was not taken of the patient wearing the frame used in devices such as the Gamma Knife® system. The present invention uses fiducial information from an actual frame, which is co-registered with the images to correlate imaging data with the radiation treatment equipment software thereby allowing for pre-planning using any type of image.

Figure 4:
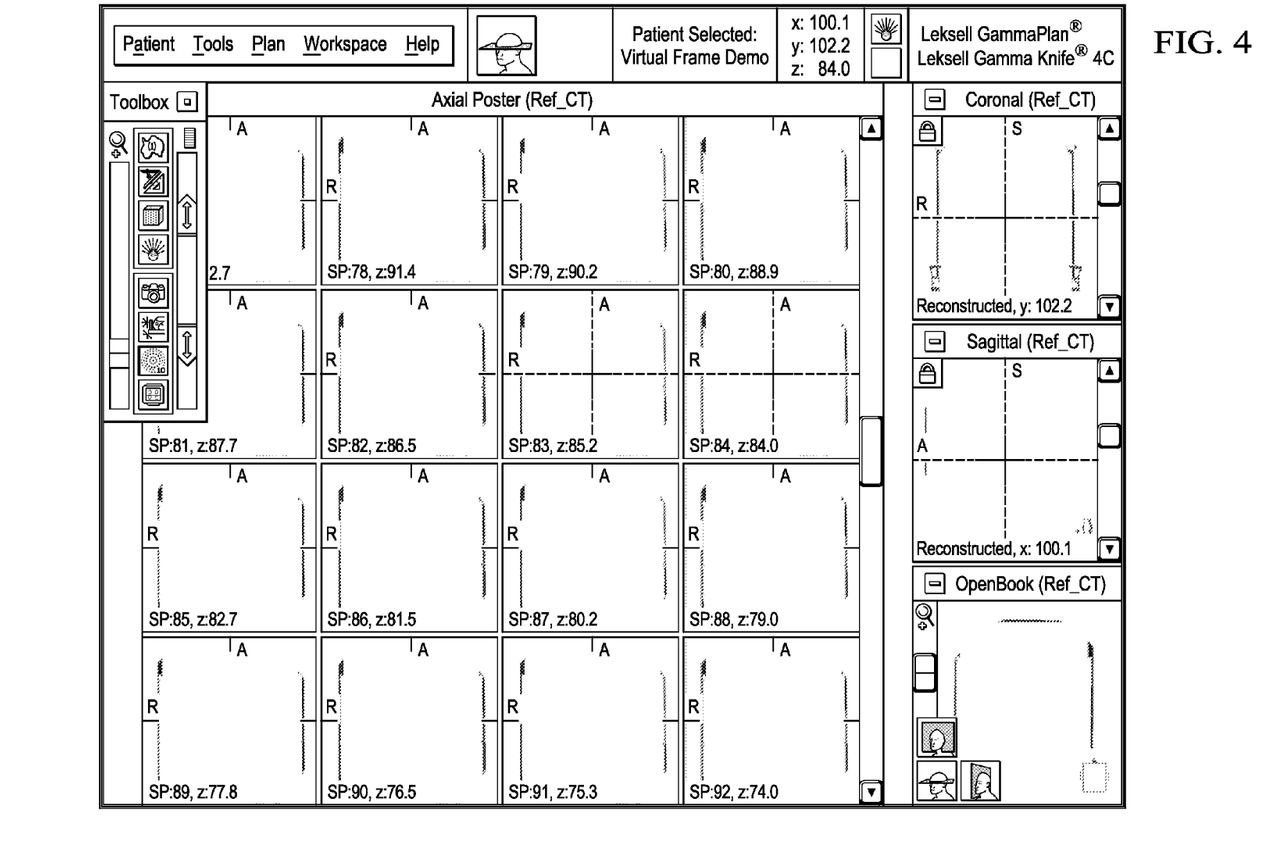
FIG. 4 is a screen shot of a CT scan of the frame registered using its fiducials as usual. The present fiducials are based on scanning a frame into the Gamma Knife® system software for the overlay step.

FIG. 4 is a screen shot of a CT scan of the frame registered using its fiducials as usual. The present fiducials are based on scanning a frame with CT fiducial box into the Gamma Knife® software for the overlay step in which there is no patient in the frame. The frame coordinates may be co-registered with the images thereby allowing accurate pre-planning.

Figure 5:
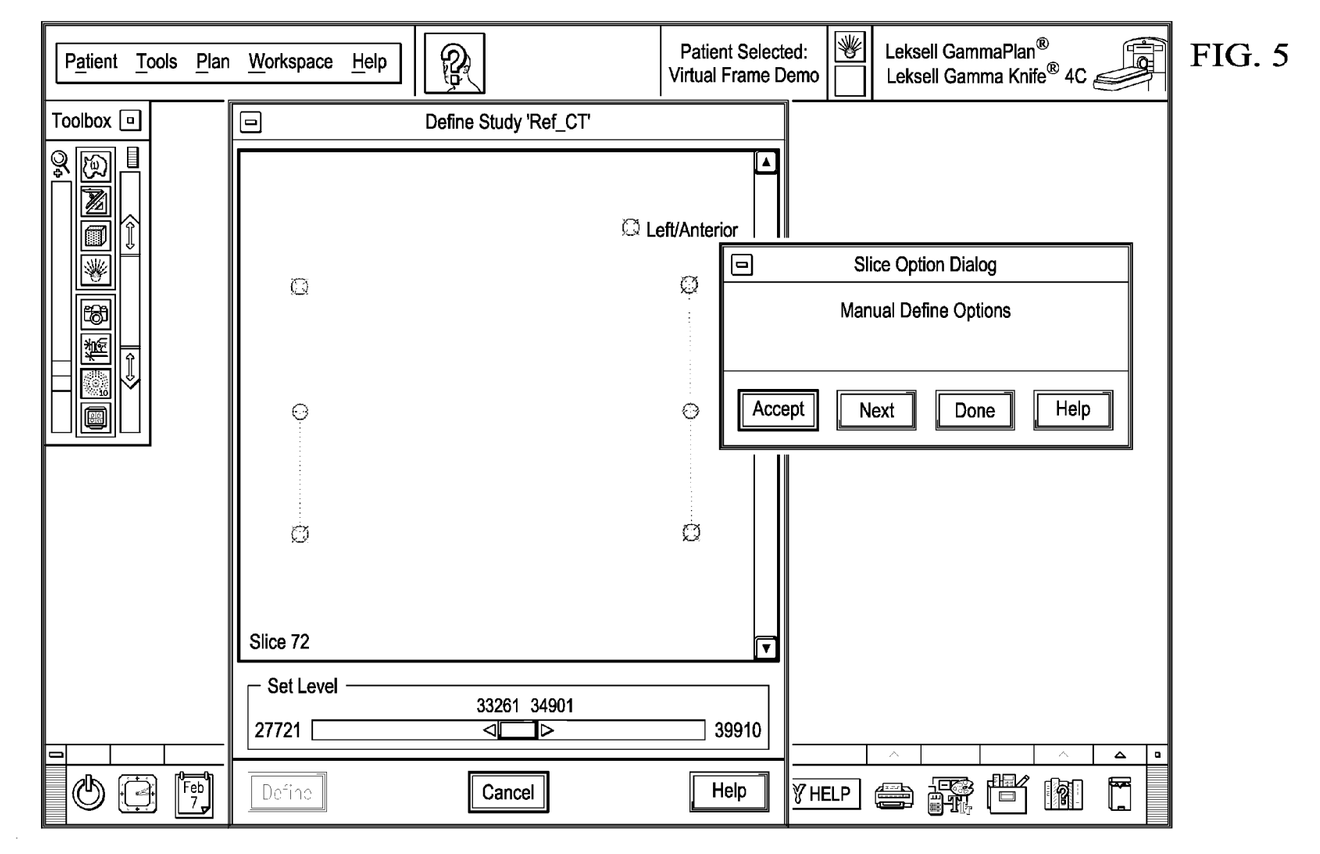
FIG. 5 is a screen shot of the Gamma Plan software that shows that the frame that includes the fiducials for coregistration has been successfully registered into the software.

FIG. 5 is a screen shot of the Gamma Plan software that shows that the frame that includes the fiducials for co-registration has been successfully registered into the software. The skilled artisan will note that various points along the length of the frame (the four corners of the frame and the position of the "N" shaped frame (the rounded marks between the four corners on the right and left side of the image. Note the relative slice designation (bottom left) that shows that the frame is at the equivalent of slice 72. The position of the left anterior (mark at the top right) is also shown based on the position of the frame.

Figure 6:
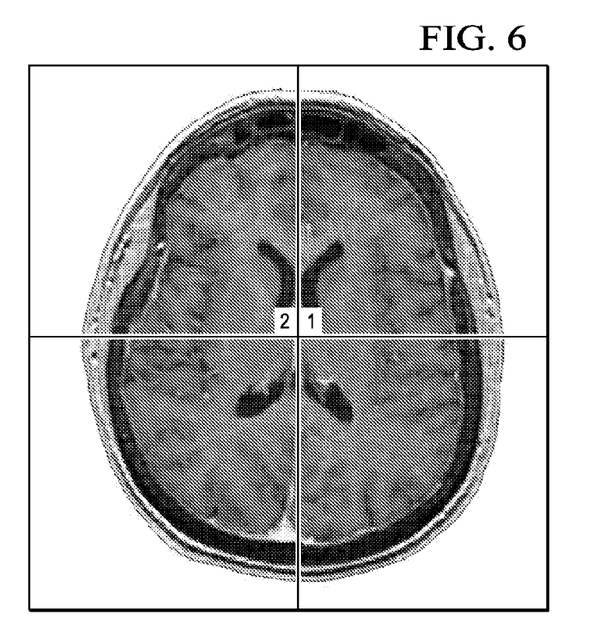
FIG. 6 is a screen shot of an MRI slice chosen in the MRI data set with maximal AP and lateral diameters to be used as the slice to correspond to the midpoint 'z=100' slice in coordinates provided by the software provided (in this example, Leksell GammaPlan). The AP and lateral diameters are measured in millimeters using the PACS system.

FIG. 6 is a screen shot of an MRI slice chosen in the MRI data set with maximal anterior-posterior (AP) and lateral diameter dimensions to be used as the slice to correspond to the midpoint 'z=100' slice in Leksell coordinates. The AP and lateral diameters are measured in millimeters using, e.g., the PACS system used to capture this image. If an equivalent measuring tool is not available, the image can be transferred to any illustration software package that does include rulers to measure the actual size of the image. These measurements may be used both for creating the right triangle and/or for calculating the skull radii.

Figure 7:
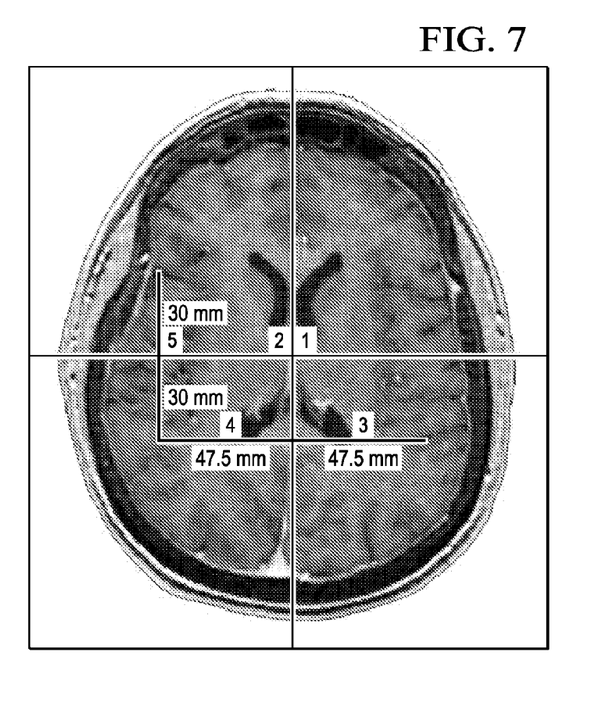
FIG. 7 is a screen shot of a right triangle that is constructed as shown with one side 60 mm and the other side 95 mm so that each side is bisected by one of the previously measured diameters. These distances are chosen because the same distances can be measured on the CT scan from the fiducials alone—the distance between the AP frame fiducials is 120 mm and that between the lateral fiducials is 190 mm, and lines with length half of these distances are easily found without requiring a measuring tool.

FIG. 7 is a screen shot of a right triangle that is constructed as shown with one side 60 mm and the other side 95 mm so that each side is bisected by one of the previously measured diameters. The skilled artisan will recognize that the shape and size may be varied, however, right triangles have proven to be a useful shape to use to transfer a dataset that includes rulers (e.g., the MRI capture software), to a system that does not include any rulers (e.g., Gamma Plan MultiView image co-registration module). While the distances may be varied, these distances were chosen for this example because the same distances can be measured on the CT or MRI scan from the fiducials alone. The anterior-posterior distance between outermost frame fiducials is 120 mm. The lateral distance between outermost fiducials is 190 mm. Lines with length half of these distances are easily found without requiring a measuring tool.

Figure 8:
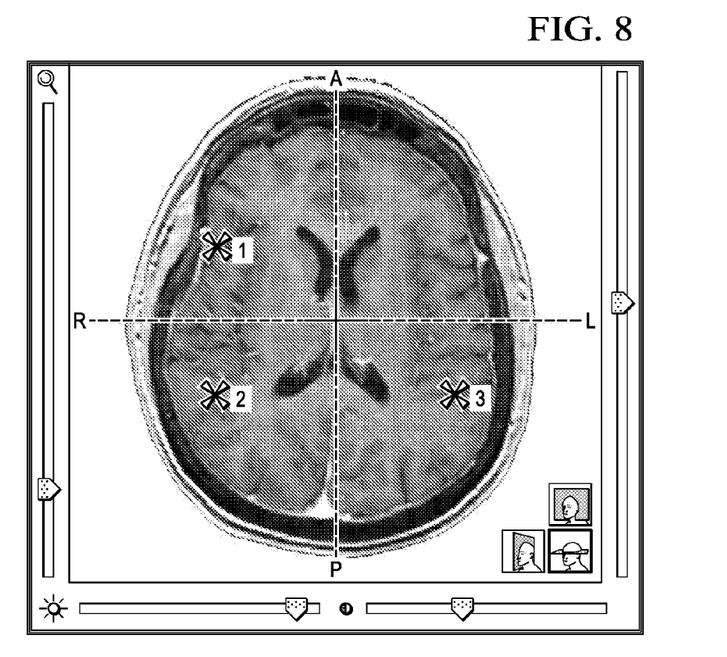
FIG. 8 is screen shot of the vertices of the triangle on the MRI scan that are registered into the co-registration software. The screen shot of the triangle is the same as that chosen on the CT scan of the frame of FIG. 7, with the same dimensions as the triangle on the MRI data using the above dimensions of the frame. Each of the vertices of the triangle is co-registered, as shown by the three set-points (numbered and within the vertices on the screen. Co-registration between the CT scan of the frame and the MRI data is then achieved using the co-registration software. Because the triangles are congruent, the resulting co-registration will preserve both distances and angles. Radiosurgery plans will therefore reflect accurate distances and angles.

FIG. 8 is a screen shot of the vertices of the triangle on the MRI scan as registered into the co-registration software. The screen shot of the triangle is the same as that chosen on the CT scan of the frame of FIG. 7 (and the image of the same slice), with the same dimensions as the triangle on the MRI data using the above dimensions of the frame. Each of the vertices of the triangle is co-registered, as shown by the three set-points (numbered and within the vertices on the screen. The positioning of the vertices is accomplished by selecting equivalent features in the image that is loaded in the Gamma Plan software. Co-registration between the CT scan of the frame and the MRI dataset is then achieved using the co-registration software. Because the triangles are congruent, the resulting co-registration will preserve both distances and angles. Radiosurgery plans will therefore reflect accurate distances and angles as well as the thickness of the slices.

Figure 9:
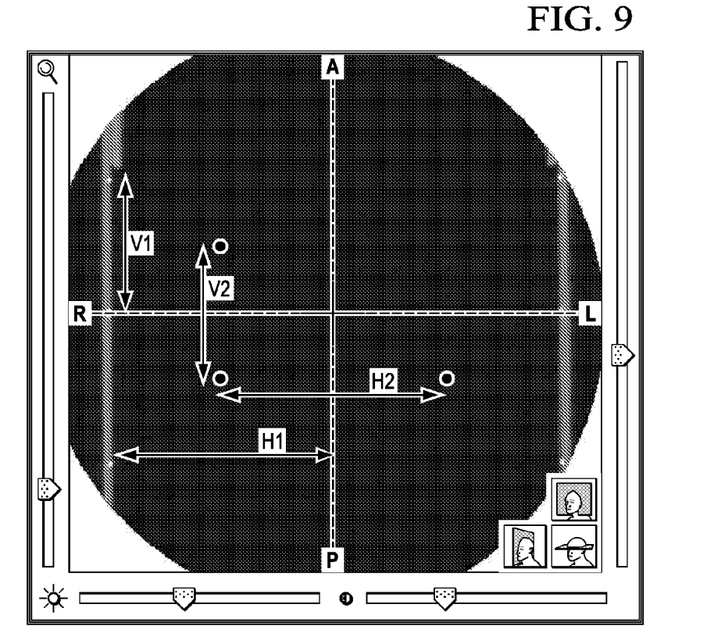
FIG. 9 is a screen shot showing co-registration of the CT frame dataset, processing is as if the data were derived for a typical Gamma Knife plan. Skull radii are calculated in an Excel spreadsheet.

FIG. 9 is a screen shot that the two data sets have been co-registered (without the MRI image) and the processing is as if the data were derived for a typical Gamma Knife plan. Next, the skull radii are calculated, e.g., using an Excel spreadsheet using the formula described hereinabove.

Figure 10:
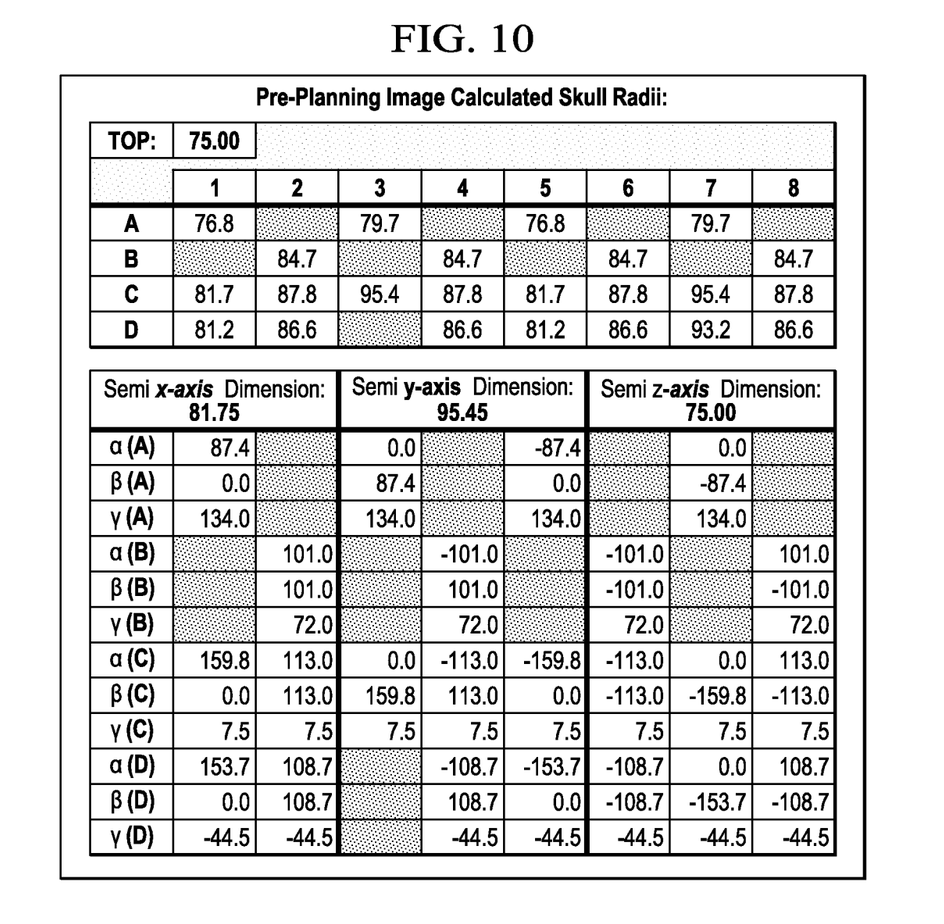
FIG. 10 is a screen shot of a spreadsheet in which skull dimension radii are calculated for insertion into the Gamma Knife software. Skull radii are entered into the Gamma Plan software.

FIG. 10 is a screen shot of a spreadsheet in which skull dimension radii are calculated for insertion into the Gamma Knife software. Skull radii are entered into the Gamma Plan software using the same format so as to maintain the co-registration.

Figure 11:
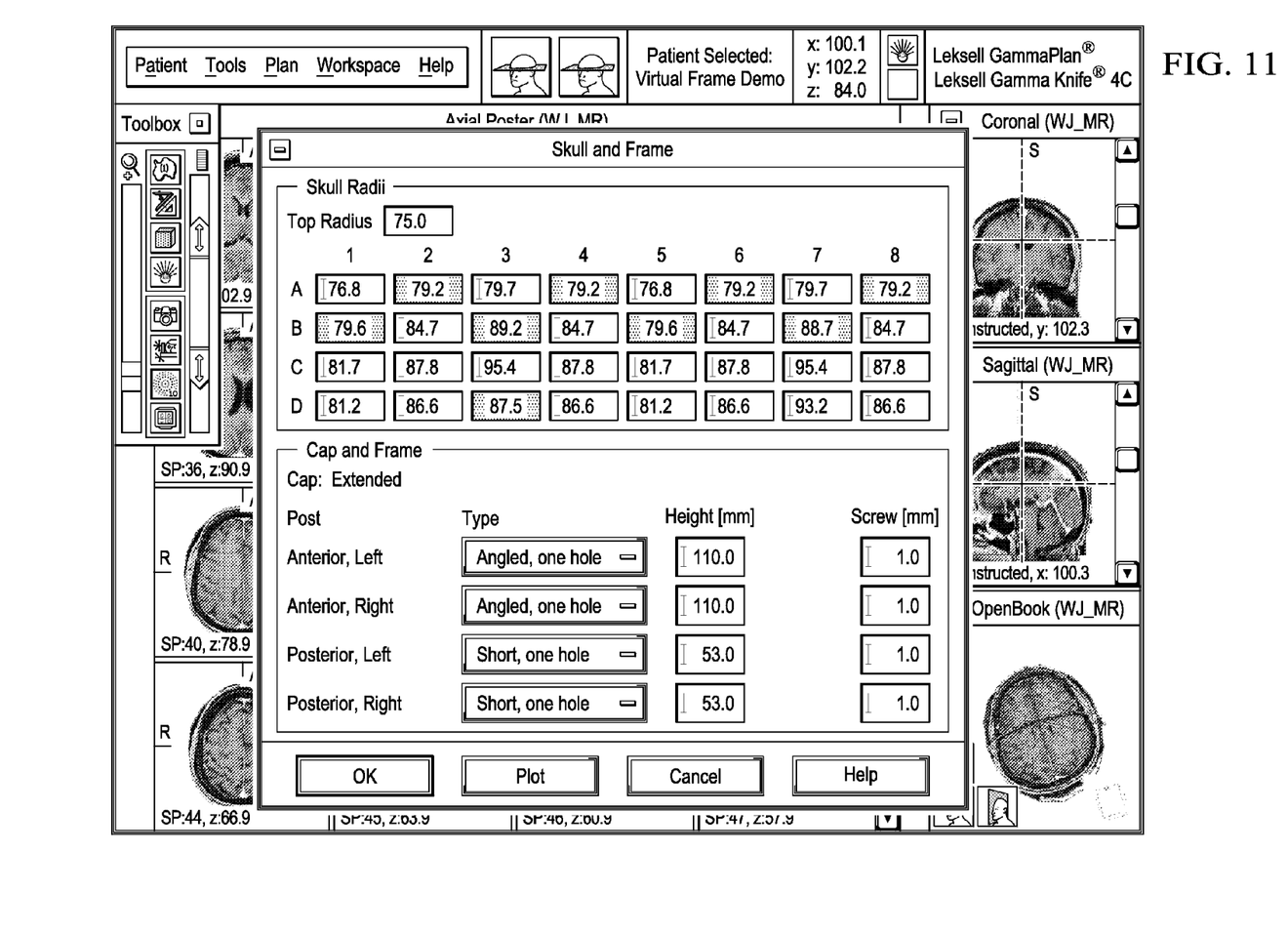
FIG. 11 is a screen shot of the combined data into which the skull radii is inserted and the data is ready for planning. Data is ready for planning.

FIG. 11 is a screen shot of the combined data into which the skull radii is inserted and the data is ready for planning. Now that the image dataset, the fiducial dataset and the skull radii has been input into the software, the patient data is now ready for planning.

Figure 12:
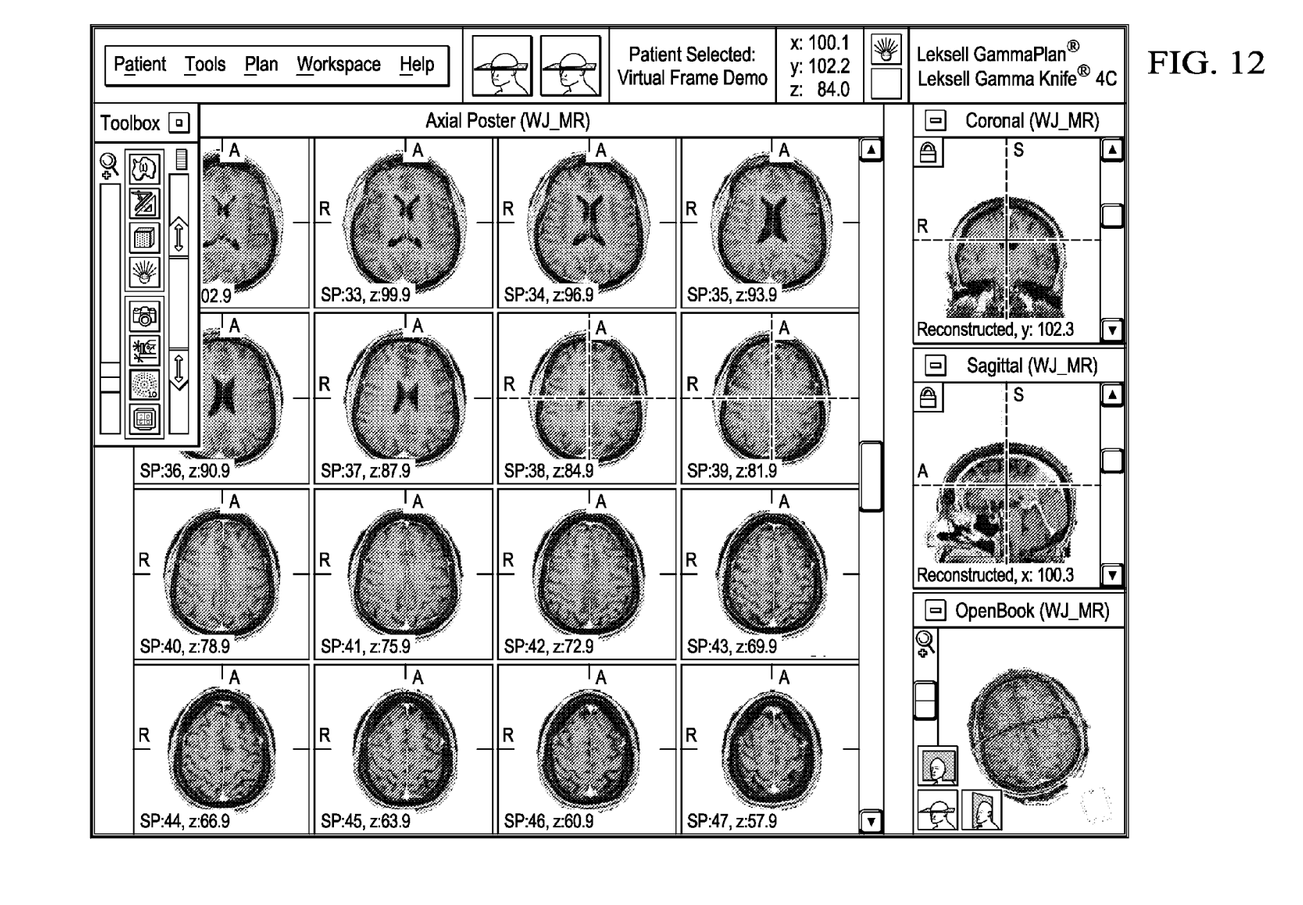
FIG. 12 is a screen shot of a comparison of the radii superimposed on the images of the MRI.

FIG. 12 is a screen shot of a comparison of the radii disposed on the images of the MRI. The skilled artisan will recognize that individual skulls may vary in size and shape, however, the present inventors have found a remarkable correlation between the vast majority of skulls and the imaging software. It has been found that the final radiation treatment plan requires minor if any modification based on actual images of slices and dimensions within an actual frame the day of treatment. In fact, it was surprising to the extent that this approximation falls well within the margin of error necessary for treatment.

Figure 13:
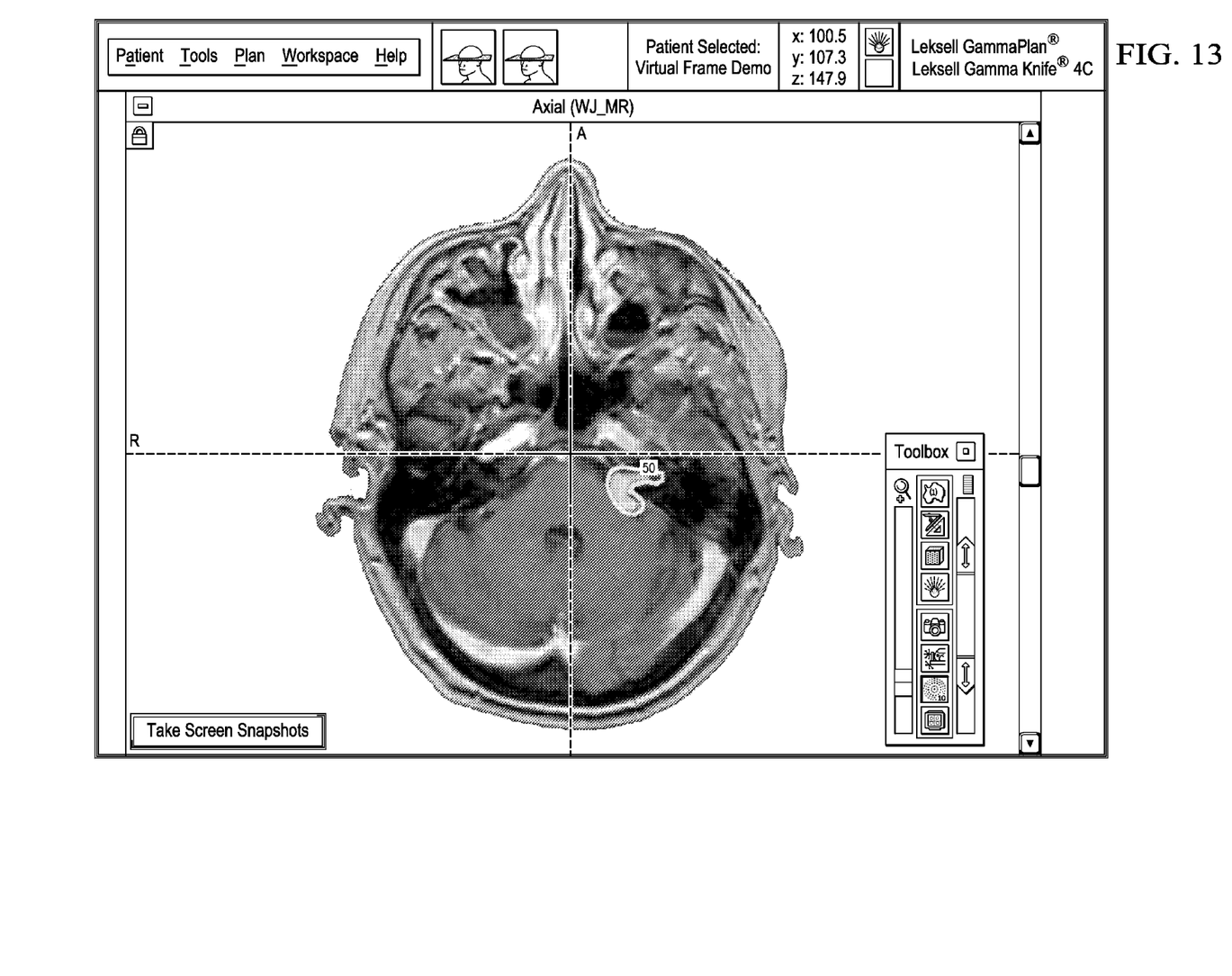
FIG. 13 is a sample plan using co-registered data provided with this example.

FIG. 13 is a sample plan using co-registered data provided with this example in which the irregular shape of the target has been input and the final treatment plan has been designed.

Figure 14:
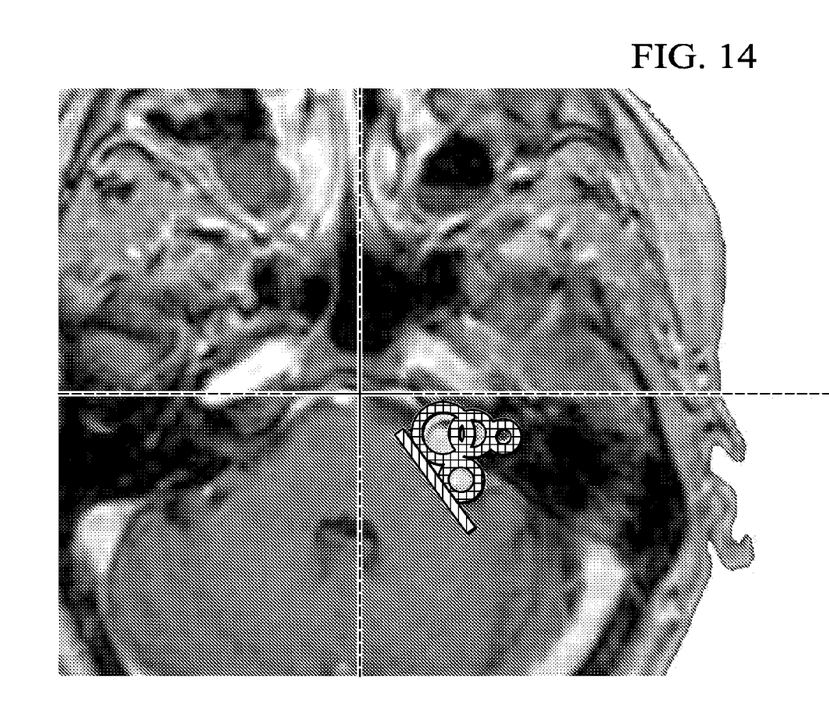
FIG. 14 is a close-up of the different overlapping targeting zones used to treat the desired location.

FIG. 14 is a close-up of a slightly different plan that includes approximate overlapping radiation targeting zones used to treat the desired location. In this treatment plan a protective zone is added to reduce radiation dose to a region of normal critical tissue near the target that the surgeon desires to protect.

Example of Virtual Frame Planning

Figure 15:
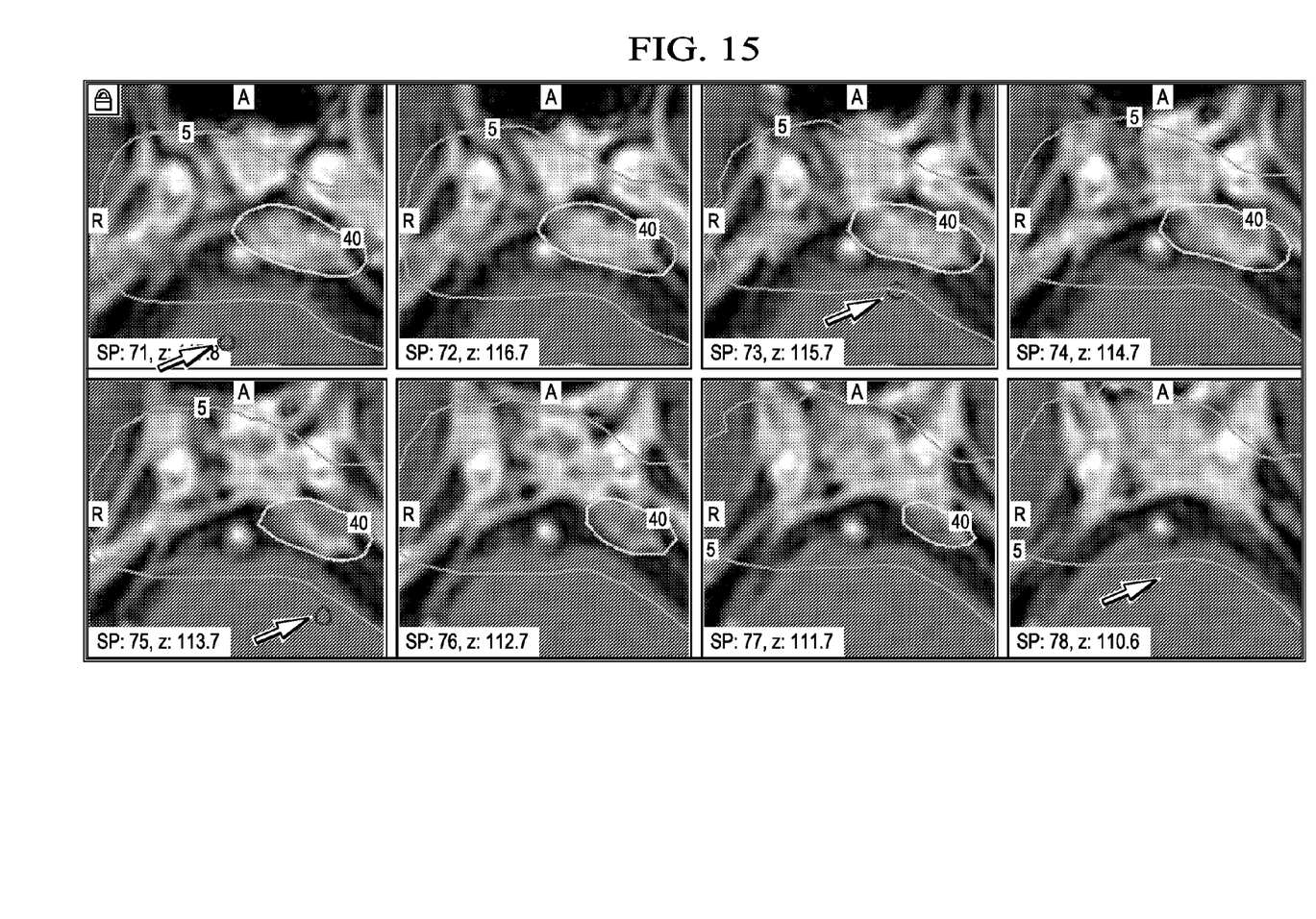
FIG. 15 underwent surgery for an intracranial chordoma (a benign tumor that is difficult to control) followed by proton beam radiotherapy in the past.

The patient in FIG. 15 underwent surgery for an intracranial chordoma (a benign tumor that is difficult to control) followed by proton beam radiotherapy in the past. MRI scans showed that a small residual nodule of tumor was growing despite the prior radiation, and so treatment was recommended. However, the risk of surgical resection of this nodule was felt to be high, as was the risk of further radiation because of prior exposure of the brainstem to radiation. It was felt that radiosurgery would be an option only if the dose to the brainstem could be kept very low, but it was uncertain whether this could be achieved with GAMMA KNIFE® radiosurgery because the tumor was located adjacent to the brainstem.

Figure 16:
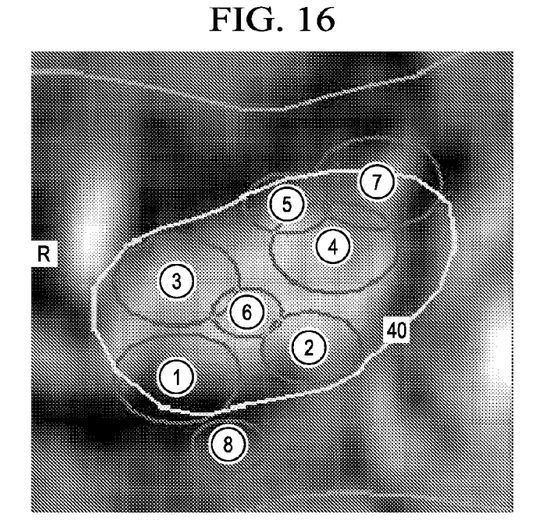
FIG. 16 shows the labeled 'Planspheres' shows the location of the shots in one slice to demonstrate the complexity of the shot arrangement.

Accordingly, a virtual frame was constructed using the patient's routine MRI studies that allowed us to try a variety of plans while attempting to deliver a high dose to the tumor while at the same time satisfy our stringent requirements for a low dose to the nearby brainstem. The figure labeled 'Plan' shows the final plan. The tumor nodule is the white area within the yellow circle 40. The yellow circle 40 is the 40% isodose line, calibrated in this case to receive a high dose of 18 Gy. The green line is the 5% isodose line, which in this case receives a very low dose of 2.25 Gy. The majority of the brainstem (the gray area below the green line) lies outside of the 5% isodose line and so receives a very low dose, as desired. The rapid falloff in dose between the tumor and the brainstem is an unusual feature of this plan, as is its construction from 4 mm collimators and the use of 4 separate shielding patterns (small arrows). FIG. 16 shows the labeled 'Planspheres' 1, 2, 3, 4, 5, 6, 7, 8 showing the location of the shots in one slice to demonstrate the complexity of the shot arrangement.

This example shows a complex plan designed according to exceedingly stringent constraints that would have been difficult, if not impossible, to construct without the time conferred by virtual framing. The patient underwent treatment without problems and the tumor has not enlarged at the time of last follow-up.

In addition to the instances described hereinabove, preplanning for Gamma Knife or other equivalent software may be used in order to allow faster planning and testing of several options. In another example, the method of the present invention includes a method of enhancing planning using Gamma Knife® software for other linear accelerator or fixed source systems by placing a virtual frame to create a series of surgical plans, tailoring the Gamma Knife plan using shot size, weights, plug patterns and the parameters of the other device so that each single shot is as close to an isocentric shot delivered by the linear accelerator as possible; transferring the Gamma Knife® coordinates to the coordinates of the other device by using three or more natural landmarks and creating a plan for the other device by creating an isocentric plan for each Gamma Knife® shot (with an analogous center) and superimposing these plans.

Finally, it is possible to use the virtual framing of the present invention to optimize treatment routines across platforms. In one example, it is possible to use the optimization algorithms of Gamma Plan to, in silico, draft a radiosurgical plan for a frameless radio surgical application in which the calculation of radiation zones using its software can take several hours per step. The Gamma Plan software can calculate the treatment radius in minutes versus hours, thereby permitting users of, e.g., Cyber Knife®, to design and test a multitude of treatment plans in hours, versus much longer using the existing planning tools for frameless radiation treatment systems. The problem is that these programs might take hours or even days to produce an optimized plan, taking too long for a patient to wait wearing a frame. While placing a virtual frame several days prior to the actual treatment provides enough time to use these lengthy algorithms, it is inefficient, inconvenient and difficult to share the software for planning while a busy radiosurgical treatment planning device is already in use.

The present invention can also be used with other optimization routines (and to develop other optimization techniques) that are available or that can be written that could potentially be used to find efficient and even unexpected plans. These routines can be used prior to the day of treatment, which is a feature provided by the in silico framing disclosed herein.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method of pre-planning a stereotactic radiosurgery comprising:
   obtaining one or more images from a patient having a target;
   adding a stereotactic frame in silico to the one or more images;
   identifying a center slice in the image to define an intermediate slice of stereotactic space that comprises, optionally, a maximum anterior-posterior and lateral diameter;
   selecting three or more points from the one or more images containing the target, wherein the three or more points comprise vertices of a right triangle with sides equal to half of the distance between a plurality of fiducial markers and the center of the stereotactic frame;
   matching the distances between the fiducial markers and the stereotactic frame;
   measuring the length, width and distance to a skull vertex in the previously selected intermediate slice image and using a parametric formula to calculate a skull radii; and
   planning an optimal stereotactic radiosurgery using the patient's actual target using actual coordinates in 3 dimensions prior to the day of surgery by creating several virtual radiosurgical coordinates and plans, thereby allowing evaluation of several plans to optimize conformality and safety.

2. The method of claim 1, further comprising the step of treating the patient based on the optimal stereotactic radiosurgery plan on a second day.

3. The method of claim 1, further comprising the step of pre-programming one or more surgical plans into the radiosurgical device based on the optimal stereotactic radiosurgery plan prior to stereotactic radiosurgery.

4. The method of claim 1, wherein the one or more images comprises one or more CT, MRI or PET images and combinations thereof.

5. The method of claim 1, wherein the one or more images is marked with one or more natural fiducials comprising bony or other anatomic landmarks, the surgical target, one or more parts of the frame or one or more pre-positioned markers.

6. The method of claim 1, wherein the stereotactic radiosurgery is performed using a gamma knife.

7. A method of pre-planning radiosurgery comprising:
   obtaining one or more images from a patient having a surgical target, the one or more images each comprising coordinates of the actual patient target in 3 dimensions;
   adding a stereotactic frame in silico to the one or more images;
   identifying a center slice in one of the one or more images to define an intermediate slice of stereotactic space that comprises, optionally, a maximum anterior-posterior and lateral diameter;
   selecting three or more points from the one or more images containing the surgical target, wherein the three or more points comprise vertices of a right triangle with sides equal to half of the distance between a plurality of fiducial markers and the center of the stereotactic frame;
   matching the distances between the fiducial markers and the stereotactic frame;
   measuring the length, width and distance to a skull vertex in the previously selected intermediate slice image and using a parametric formula to calculate a skull radii;
   planning an optimal stereotactic radiosurgery using the patient's actual target within a virtual frame using actual coordinates in 3 dimensions prior to the day of surgery by executing virtually several surgical plans using the patient's actual target and virtual frame image, wherein the plan maximizes target exposure;
   pre-programming one or more of the plans into the linear accelerator stereotactic radiosurgery device; and
   treating the patient based on the optimal stereotactic radiosurgery plan.

8. The method of claim 7, further comprising the step of pre-programming one or more surgical plans into the radiosurgical device based on the optimal stereotactic radiosurgery plan prior to stereotactic radiosurgery.

9. The method of claim 7, wherein the one or more images comprise one or more CT, MRI or PET images and combinations thereof.

10. The method of claim 7, wherein the one or more images are marked with one or more natural fiducials comprising bony or other anatomic landmarks, the surgical target, one or more parts of the frame or one or more pre-positioned markers.

11. The method of claim 7, wherein the datasets are fused by adding the stereotactic frame as an overlay to the patient dataset and then the fused dataset is imported at the planning step.

12. The method of claim 7, wherein the stereotactic frame and patient datasets are co-registered directly.

* * * * *